United States Patent

Grüning et al.

Patent Number: 5,491,245
Date of Patent: Feb. 13, 1996

[54] METHOD FOR THE SYNTHESIS OF AMPHOTERIC SURFACTANTS

[75] Inventors: Burghard Grüning; Christian Weitemeyer, both of Essen, Germany

[73] Assignee: Th. Goldschmidt AG, Essen, Germany

[21] Appl. No.: 213,355

[22] Filed: Mar. 15, 1994

[30] Foreign Application Priority Data

Mar. 26, 1993 [DE] Germany .................. 43 09 900.9

[51] Int. Cl.⁶ .................................................. C07C 231/12
[52] U.S. Cl. ........................ 554/68; 554/52; 554/59
[58] Field of Search ............................ 554/52, 59, 68, 554/67

[56] References Cited

FOREIGN PATENT DOCUMENTS 223689  8/1959  Australia ............................... 554/59
3939264  5/1991  Germany .

*Primary Examiner*—José G. Dees
*Assistant Examiner*—Deborah D. Carr
*Attorney, Agent, or Firm*—Anderson Kill Olick & Oshinsky

[57] ABSTRACT

A method for the synthesis of amphoteric surfactants by the reaction of amines with chloroacetic acid or its salts in aqueous solution at an elevated temperature, consists of reacting compounds of the general formula $$R^1-R^2-N-[(CH_2)_n-N-]_p R^3$$
$$\phantom{R^1-R^2-}|\phantom{-[(CH_2)_n-}|$$
$$\phantom{R^1-R^2-}H\phantom{-[(CH_2)_n-}H$$

with chloroacetic acid at temperatures ranging from 115° to 180° C., until the chloroacetic acid content is less than 10 ppm.

4 Claims, No Drawings

METHOD FOR THE SYNTHESIS OF AMPHOTERIC SURFACTANTS

FIELD OF INVENTION

The invention relates to a method for the synthesis of amphoteric surfactants by the reaction of amines with chloroacetic acid or its salts in aqueous solution at an elevated temperature.

More particularly, the invention relates to a method which enables the synthesis of amphoteric surfactants having a very low content of organically linked chlorine, particularly of sodium monochloroacetate and sodium dichloroacetate.

BACKGROUND INFORMATION AND PRIOR ART

Amphoteric surfactants are used on a large scale for the preparation of toiletries, particularly for the preparation of shampoos. One therefore strives to synthesize the amphoteric surfactants free of impurities, which can cause skin irritations or are undesirable in some other way for physiological reasons. These include also residual amounts of compounds with organically linked chlorine, particularly sodium dichloroacetate, which is introduced directly into the end product along with the chloroacetic acid raw material or its salts. Attempts to reduce the content of sodium dichloroacetate by employing longer reaction times or higher pH values, did not lead to a significant decrease in the dichloroacetate content. The use of higher pH values, particularly those above 10.5, entails the risk of increasingly decomposing the product.

The German Offenlegungsschrift 39 39 264 relates to a method for lowering the residual content of free alkylating agent in aqueous solutions of amphoteric or zwitterionic surfactants, with the requirement that the solutions are given an aftertreatment with ammonia, amino acid with 2 to 8 carbon atoms or oligopeptide. By means of this aftertreatment, the residual content of free alkylating agent, particularly of chloroacetic acid, is to be reduced to values below 0.01% by weight (based on the solids content). A significant disadvantage of this method lies, however, therein that an additional process step is required. A further disadvantage can be seen therein that the products of the reaction of the alkylating agent with ammonia, an amino acid or an oligopeptide remain in the process product as impurity.

OBJECT OF THE INVENTION

An object of the present invention is a method of synthesizing an amphoteric surfactant having a greatly reduced content of impurities, particularly of compounds with organically linked chlorine, such as sodium monochloroacetate and sodium dichloroacetate. The method avoids a separate, additional process step for purifying the products.

SUMMARY OF THE INVENTION

The inventive method is characterized in that compounds of the general formula

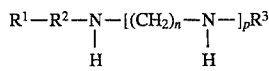

wherein $R^1$ is a saturated or unsaturated alkyl group with 7 to 19 carbon atoms, $R^2$ is a $-(CH_2)_q-$, $-O(CH_2)_q-$ or $-C=O$ group (q=1 to 3), is a hydrogen or $-CH_2CH_2-OH$ group, n has a numerical value of 2 or 3 and p has a numerical value of 1 to 4, are reacted with, in relation to the aforementioned amines, at least equimolar amounts of chloroacetic acid or its salts at temperatures ranging from 115° to 180° C., until the chloroacetic acid content is less than 10 ppm.

In a preferred variation of the method, the amine is partially or completely carboxymethylated in a first step at 80° to 100° C. In the formula

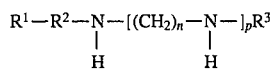

for the starting compound, $R^1$ is a saturated or an unsaturated alkyl group with 7 to 19 carbon atoms. Preferably, $R^1$ is a saturated or unsaturated alkyl group with 9 to 17 carbon atoms.

$R^2$ is a $-(CH_2)_q-$, $-O(CH_2)_q-$ or $-C=O$ group, wherein the subscript q has a numerical value of 1 to 3. Preferably, the $R^2$ group is a $-(CH_2)_2-$ or a $-O(CH_2)_3$ group.

$R^3$ is a hydrogen or $-CH_2CH_2OH$ group. In this case, $R^3$ has the meaning of a hydrogen group.

n has a numerical value of 2 or 3 and preferably of 2. p has a numerical value of 2 to 4 and preferably of 1 to 2.

Preferably, the reaction is carried out at a temperature of 120° C. to 160° C., particularly at a temperature of 120° to 140° C. The reaction time, after which the content of monochloroacetic acid and dichloroacetic acid is less than 10 ppm, is about 1 to 10 hours, depending on the temperature.

It may be of advantage to carboxymethylate the amine partially or completely first in a preliminary reaction at 80° to 100° C. and to split off the organically linked chlorine only subsequently at an elevated temperature of at least 115° C. Since the carboxymethylation reaction and the splitting off reaction of the organically linked chlorine proceed concurrently at the elevated temperature, an excess amount of halogen alkyl carboxylic acid must be used if the reaction is carried out in one step. However, if the carboxymethylation reaction is already carried out partially or completely in a first step at a temperature of 80° to 100° C., it is possible to carry out the reaction with stoichiometric amounts or with only a slight excess of halogen alkyl carboxylic acid.

In view of the temperatures selected, it is necessary to work in a closed system, such as an appropriately dimensioned autoclave with stirrer.

The lower limit of the temperature range of 115° C. is determined by the onset of the splitting reaction of sodium dichloroacetate. Below this temperature, there is no splitting or the splitting requires too much time to be acceptable for a method that is to be carried out in an economic manner. The upper limit of the temperature range of 180° C. is determined by the onset of decomposition of the process products or of the reactants.

With the inventive method, it is possible to lower the content of sodium monochloroacetate and sodium dichloroacetate in the betaine solution below the limit of 10 ppm.

The inventive method has the advantage that reagents, which split the organic chlorine compounds and contaminate the product, do not have to be added to the product.

Examples of compounds, obtainable by the inventive method, are amphoglycinates of the general formula

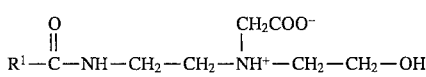

$$R^1-\overset{O}{\overset{\|}{C}}-NH-CH_2-CH_2-\overset{|}{N}H^+-CH_2-CH_2-OH$$
(with CH₂COO⁻ on the N⁺)

and polybetaines

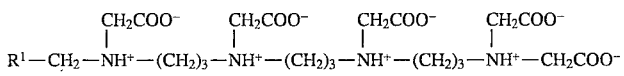

$$R^1-CH_2-NH^+-(CH_2)_3-NH^+-(CH_2)_3-NH^+-(CH_2)_3-NH^+-CH_2COO^-$$
(each N⁺ bears a CH₂COO⁻)

and

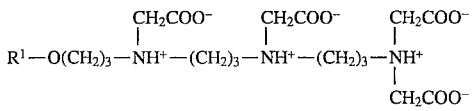

$$R^1-O(CH_2)_3-NH^+-(CH_2)_3-NH^+-(CH_2)_3-NH^+$$
(each N⁺ bears a CH₂COO⁻)

The $R^1$ groups can have a uniform molecular weight or a molecular weight distribution. Examples of the $R^1$ group are:

$$CH_3-(CH_2)_8-, CH_3-(CH_2)_{10}-, CH_3(CH_2)_{6.5}-CH=CH-(CH_2)_7-, CH_3-(CH_2)_{16}-$$

or, derived from the fatty acid distribution of natural fats, a mixture of approximately 30% by weight of $CH_3-(CH_2)_{14}-$ and approximately 70% by weight of $CH_3-(CH_2)_{16}-$ in the case of hydrogenated beef tallow or a mixture of approximately 5% by weight of $CH_3(CH_2)_6-$; approximately 5% by weight of $CH_3(CH_2)_8-$; approximately 50% by weight of $CH_3(CH_2)_{10}-$; approximately 15% by weight of $CH_3(CH_2)_{12}-$; approximately 15% by weight of $CH_3(CH_2)_{14}-$; and approximately 10% by weight of $CH_3(CH_2)_{16}-$ in the case of hydrogenated coconut oil.

The inventive compounds can be used in various ways as gentle surfactants in cosmetics, where they are used primarily as secondary surfactants in admixture with anionic surfactants, or also with further gentle surfactants such as betaines and/or nonionic surfactants, such as ethoxylated glycerin, sorbitol and other sugar esters, as well as with sugar surfactants, such as alkyl polyglycosides. Furthermore, they can also be used as textile auxiliaries, particularly as antistats and as materials for influencing the handle of textiles.

In the following examples, the synthesis of the compounds by the inventive method is explained in greater detail.

In the examples, amines of the following general formula are used:

Formula A:

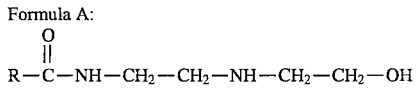

$$R-\overset{O}{\overset{\|}{C}}-NH-CH_2-CH_2-NH-CH_2-CH_2-OH$$

in admixture with

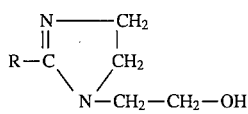

Formula B:

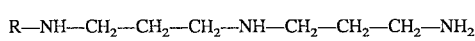

$$R-NH-CH_2-CH_2-CH_2-NH-CH_2-CH_2-CH_2-NH_2$$

Formula C:

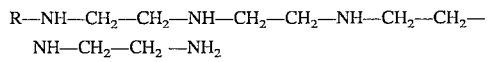

$$R-NH-CH_2-CH_2-NH-CH_2-CH_2-NH-CH_2-CH_2-NH-CH_2-CH_2-NH_2$$

As sodium monochloroacetate, a product of conventional, commercial quality is used, which contains about 0.1% by weight of sodium dichloroacetate as impurity. The contents of monochloroacetic acid and dichloroacetic acid are determined in the following way with the help of a gas chromatographic analysis:

The product (0.5 g ±0.1 mg) is homogenized with 2.5 mL of ethanol for one minute in an ultrasonic bath, mixed with 0.25 mL of concentrated sulfuric acid and homogenized once again. The mixture is heated for 15 minutes at 50° C., tooled, mixed with 5 mL of 5% by weight of aqueous sodium chloride solution and 5 mL of cyclohexane and stirred for 5 minutes. After the phases have separated, a sample is taken from the organic phase and injected into a gas chromatograph. The analysis is carried with a Hewlett Packard (HP) 5890 Gas Chromatograph (Series II) or an HP-20-M capillary column in conjunction with an EC detector under the following conditions: temperature gradient from 75° to 200° C.=10° C. per minute, injector 225° C., detector 240° C.

EXAMPLE 1

Synthesis of an Amphoglycinate From the Hydroxyethylaminoethylamide of Coconut Fatty Acids and 1 Mole of Sodium Chloroacetate in Two Steps A hydroxyethylaminoethylamide of coconut fatty acids having the general formula A (300 g, 1 mole) from hydrogenated coconut fatty acids with a nitrogen value of 4.4% by weight, as determined by titration with 0.1N hydrochloric acid, is dispersed in 428 mL of water and mixed at 60° C. with 128.2 g (1.1 moles) of sodium chloroacetate. The reaction mixture is heated to 95° C. Due to the reaction, the pH drops and, as soon as necessary, is held at 8.5 by the addition of 40% by weight of sodium hydroxide solution. After 7 hours, a sample is taken, cooled and analyzed. The following values are determined:
Solids: 50%
NaCl: 7.5%
Water: 50%
Sodium chloroacetate: 1.3 ppm
Sodium dichloroacetate: 125 ppm The bulk of the formulation is subsequently heated for 6 hours at 140° C. in a 250 mL laboratory autoclave, a pressure of 2.5 bar being obtained. At the end of the reaction, the product is cooled and analyzed once more. The following values are obtained:
Solids: 50%
NaCl: 7.5%
Water: 50%
Sodium chloroacetate: 0.1 ppm
Sodium dichloroacetate: 5.2 ppm

EXAMPLE 2

Synthesis of an Amphoglycinate From the Hydroxyethylaminoethylamide of Coconut Fatty Acids and 1 Mole of Sodium Chloroacetate in One Step The method of Example 1 is repeated. However, after the starting products are added together and 10.2 mL of 40% by weight sodium hydroxide solution are added, the reaction formulation is added directly to the laboratory autoclave and heated for 6 hours at 140° C. At the end of the reaction, the product is cooled and analyzed. The following values are obtained:
Solids: 50%
NaCl: 7.5%
Water: 50%
Sodium chloroacetate: 0.2 ppm
Sodium dichloroacetate: 3.4 ppm

EXAMPLE 3

Synthesis of an Amphoglycinate From the Hydroxyethylaminoethylamide of Coconut Fatty Acids and 2 Moles of Sodium Chloroacetate in Two Steps The hydroxyethylaminoethylamide of coconut fatty acids described in Example 1 (300 g, 1 mole) is dispersed in 556 mL of water and mixed with 256.4 g (2.2 moles) of sodium chloroacetate at 60° C. The reaction mixture is heated with stirring to 95° C. and, after the pH drops, is kept at a pH of 8.5 by the addition of 40% by weight of sodium hydroxide solution and heated for a further 6 hours with stirring at 95° C. A sample is taken from the reaction formulation, cooled and analyzed. The following values are determined:
Solids: 50%
NaCl: 11.5%
Water: 50%
Sodium chloroacetate: 0.9 ppm
Sodium dichloroacetate: 166 ppm The bulk of the formulation is subsequently heated for 6 hours at 140° C. in a 250 mL laboratory autoclave, a pressure of 2.5 bar being obtained. At the end of the reaction, the sample is cooled and analyzed once more. The following values are determined:
Solids: 50%
NaCl: 11.5%
Water: 50%
Sodium chloroacetate: 0.3 ppm
Sodium dichloroacetate: 0.4 ppm

EXAMPLE 4

Synthesis of a Polyamphoglycinate From Tallow

Dipropylenetriamine and 4 Moles of Sodium Chloroacetate

Tallow dipropylenetriamine of the general formula B (370 g, 1 mole), the long-chain alkyl R group of which consists of approximately 30% $C_{16}H_{33}$ and approximately 70% of $C_{18}H_{37}$, with a nitrogen value, determined by titration with 0.1N HCl, of 11.3% by weight, is dispersed in 1305 mL of water and mixed at 70° C. with 500 g (4.3 moles) of sodium chloroacetate. The reaction mixture is heated with stirring to 95° C. After the pH drops, the reaction mixture is kept at a pH of 8.5 by the addition of 40% by weight of sodium hydroxide solution and heated for a further 6 hours with stirring at 95° C. A sample is taken from the formulation, cooled and analyzed. The following values are determined:
Solids: 40%
NaCl: 11.5%
Water: 60%
Sodium chloroacetate: 2.2 ppm
Sodium dichloroacetate: 234 ppm The bulk of the formulation is subsequently heated for 2 hours at 180° C. in a 250 mL laboratory autoclave, a pressure of 7.5 bar being obtained. At the end of the reaction, the product is cooled and analyzed once more. The following values are determined:
Solids: 40%
NaCl: 11.5%
Water: 60%
Sodium chloroacetate: 0.4 ppm
Sodium dichloroacetate: 1.2 ppm

EXAMPLE 5

Synthesis of a Polyamphoglycinate From Lauryl

Tetraethylenepentamine and 6 Moles of Sodium Chloroacetate

Lauryl tetraethylenepentamine of the general average formula C (358 g, 1 mole), the long-chain alkyl R group of which consists to the extent of more than 90% of $C_{12}H_{25}$ and which has a nitrogen value of 18.9% by weight as determined by titration with 0.1N HCl, is dispersed in 1673 mL of water and mixed at 60° C. with 757 g (6.5 moles) of sodium chloroacetate. The reaction mixture is heated to 95° C. with continuing stirring and, after the pH falls to 8.5, which is the case after 1 hour, maintained at a pH of 10 by the addition of 40% by weight of sodium hydroxide solution. The reaction mixture is subsequently heated for 4 hours at 140° C. in a laboratory autoclave. At the end of the reaction, the product is cooled and analyzed. The following values are determined:
Solids: 40%
NaCl: 13.5%
Water: 60%
Sodium chloroacetate: 1.5 ppm
Sodium dichloroacetate: 0.9 ppm

We claim:
1. A method for the synthesis of an amphoteric surfactant by reacting amines with chloroacetic acid or its salts in aqueous solution at an elevated temperature, comprising that compounds of the general formula

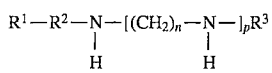

wherein
R¹ is a saturated or unsaturated alkyl group with 7 to 19 carbon atoms,
R² is a $-(CH_2)_q-$, $-O(CH_2)_q-$ or $-C=O$ group (q =1 to 3), is a hydrogen or $-CH_2H_2-OH$ group,
n has a numerical value of 2 or 3 and
p has a numerical value of 1 to 4,
are reacted with at least equimolar amounts of chloroacetic acid salts at a temperature ranging from about between 115° and 180° C., until the chloroacetic acid content is less than 10 ppm.

2. The method of claim 1, further comprising that the amine is carboxymethylated partially or completely at about between 80° and 100° C.

3. The method of claim 1, further comprising that the reaction is carried out a temperature of about between 120° and 160° C.

4. The method of claim 1, further comprising that the reaction is carried out at a temperature of about between 120° and 140° C.

* * * * *